United States Patent [19]

Krämer et al.

[11] Patent Number: 4,639,462
[45] Date of Patent: * Jan. 27, 1987

[54] HETEROCYCLO-HYDROXYALKYL-AZOLYL DERIVATIVES AND USE AS FUNGICIDES

[75] Inventors: Wolfgang Krämer, Wuppertal; Karl H. Büchel, Burscheid; Graham Holmwood; Erik Regel, both of Wuppertal; Paul Reinecke, Leverkusen; Wilhelm Brandes, Leichlingen, all of Fed. Rep. of Germany

[73] Assignee: Bayer Aktiengesellschaft, Leverkusen, Fed. Rep. of Germany

[ * ] Notice: The portion of the term of this patent subsequent to Nov. 11, 2003 has been disclaimed.

[21] Appl. No.: 547,807

[22] Filed: Nov. 1, 1983

[30] Foreign Application Priority Data

Nov. 15, 1982 [DE] Fed. Rep. of Germany ....... 3242252

[51] Int. Cl.⁴ .................... A01N 43/50; A01N 43/61; C07D 233/60; C07D 249/08
[52] U.S. Cl. ..................... 514/383; 514/184; 514/399; 548/101; 548/262; 548/336
[58] Field of Search ....... 548/101, 262, 336; 424/245, 269, 273 R; 514/184, 383, 399

[56] References Cited

U.S. PATENT DOCUMENTS 4,496,388  1/1985  Clough .................................. 71/92

FOREIGN PATENT DOCUMENTS 0044407  1/1982  European Pat. Off. ............ 548/262
0062236  10/1982 European Pat. Off. ............ 548/262
0078594  5/1983  European Pat. Off. ............ 548/262
0084834  8/1983  European Pat. Off. ............ 548/262
0085333  8/1983  European Pat. Off. ............ 548/262
3018866  11/1981 Fed. Rep. of Germany ...... 548/262

Primary Examiner—Richard L. Raymond
Attorney, Agent, or Firm—Sprung Horn Kramer & Woods

[57] ABSTRACT

Heterocyclyl-hydroxyalkyl-azolyl derivatives of the formula

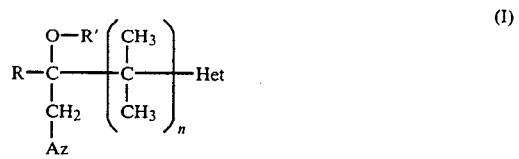

in which
Az represents 1,2,4-triazol-1-yl, 1,2,4-triazol-4-yl or imidazol-1-yl,
Het represents optionally substituted dioxolanyl or 1,3-dioxanyl,
R represents alkyl, optionally substituted phenyl, optionally substituted phenylalkyl, optionally substituted phenoxyalky, optionally substituted phenylthioalkyl, optionally substituted cycloalkyl, optionally substituted cycloalkylalkyl, alkenyl, optionally substituted phenylalkenyl, optionally substituted cyclohexylalkenyl, furyl, naphthyloxymethyl or azolylalkyl,
R' represents hydrogen, optionally substituted alkyl or alkenyl and
n represents the number 0 or 1, or addition products thereof with acids or metal salts, which possess fungicidal activity.

12 Claims, No Drawings

HETEROCYCLO-HYDROXYALKYL-AZOLYL DERIVATIVES AND USE AS FUNGICIDES

The present invention relates to new hydroxyalkylazdylyl derivatives substituted by heterocyclic substituents, sveral processes for their preparation and their use as fungicides.

It has already been disclosed that certain hydroxyethyl-azolyl derivatives, such as, for example, 3,3-dimethyl-1-phenoxy-2-(1,2,4-triazol-1-yl-methyl)-2butanol or 1-(2-chloro-4-fluorophenoxy)-3,3-dimethyl-1(1,2,4-triazol-1-yl-methyl)-2-butanol or 1-(4-chlorophenoxy)-2-(2,4-dichlorophenyl)-3-(imidazol-1-yl)-2-propanol, have fungicidal properties (compare DE-OS [German Published Specification] No. 3,018,866. However, the activity of these compounds is not always completely satisfactory, especially when low amounts and concentrations are applied.

New hydroxyalkyl-azolyl derivatives substituted by heterocyclic substituents, of the general formula

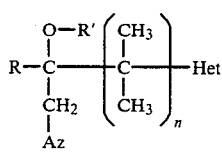

(I)

in which
Az represents 1,2,4-triazol-1-yl, 1,2,4-triazol-4-yl or imidazol-1-yl,
Het represents optionally substituted dioxolanyl or 1,3-dioxanyl,
R represents alkyl, optionally substituted phenyl, optionally substituted phenylalkyl, optionally substituted phenoxyalkyl, optionally substituted phenylthioalkyl, optionally substituted cycloalkyl, optionally substituted cycloalkylalkyl, alkenyl, optionally substituted phenylalkenyl, optionally substituted cyclohexylalkenyl, furyl, naphthyloxymethyl or azolylalkyl,
R' represents hydrogen, optionally substituted alkyl or alkenyl and
n represents the number 0 or 1, and acid addition salts and metal salt complexes thereof, have been found.

In some cases, the compounds of the formula (I) have an asymmetric carbon atom, and they can therefore be obtained in the two optical isomer forms.

It has furthermore been found that the hydroxyalkyl-azolyl derivatives substituted by heterocyclic substituents, of the formula (I), are obtained by a process in which
(a) oxiranes of the formula (II)

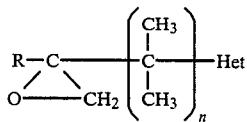

(II)

in which
Het, R and n have the abovementioned meaning, are reacted with azoles of the formula (III)

M—Az (III)

in which

Az has the abovementioned meaning and
M represents hydrogen or an alkali metal salt, in the presence of a diluent and, if appropriate, in the presence of a base, or
(b) azolo-ketones of the formula (IV)

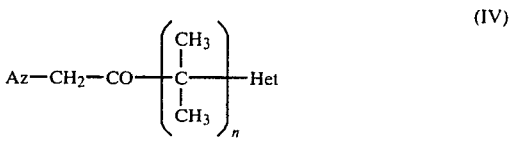

(IV)

in which
Az, Het and n have the abovementioned meaning, are reacted with an organomagnesium compound of the formula (V)

R—Mg—X (V)

in which
R has the abovementioned meaning and
X represents chlorine, bromine or iodine, in the presence of a diluent, or
(c) azolo-oxiranes of the formula (VI)

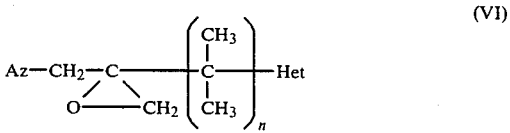

(VI)

in which
Az, Het and n have the abovementioned meaning, are reacted with optionally substituted phenols and thiophenols and with organometallic compounds of the formula (VII)

R—Me (VII)

in which
R has the abovementioned meaning and
Me represents an alkali metal or —Mg—X, wherein
X has the abovementioned meaning, in the presence of a diluent and if appropriate in the presence of a base, and subsequently, if appropriate,
(d) the hydroxy compounds (wherein R' in formula (I) represents hydrogen) obtained according to process (a), (b) or (c) is converted into the alkali metal alcoholate in the presence of a diluent, and this product is reacted with a halide to give the corresponding ether derivatives (wherein R' in formula (I) represents an optionally substituted alkyl group or an alkenyl group).

If desired, an acid or a metal salt can then be added on to the compounds of the formula (I) thus obtained.

The new hydroxyalkyl-azolyl derivatives substituted by heterocyclic substituents, of the formula (I), have powerful fungicidal properties. Surprisingly, the compounds according to the invention exhibit a more powerful action than the hydroxyethyl-azolyl derivatives 3,3-dimethyl-1-phenoxy-2-(1,2,4-triazol-1-ly-methyl)-2-butanol, 1-(2-chloro-4-fluorophenoxy)-3,3-dimethyl-2-(1,2,4-triazol-1-ly-methyl)-2-butanol or 1-(4-chlorophenoxy)-2-(2,4-dichlorophenyl)-3-(imidazol-1-ly)-2-propanol, which are known from the prior art and are closely related compounds structurally and from the point of view of their action. The substances according to the invention thus represent an enrichment of the art.

Formula (I) provides a general definition of the hydroxyalkyl-azolyl derivatives, substituted by heterocyclic substituents, according to the invention. Preferably, in the formula, Az represents 1,2,4-triazol-1-ly, 1,2,4-triazol-4-ly or imidazol-1-ly;

Het represents dioxolan-2-ly or 1,3-dioxanyl, each of which is optionally monosubstituted or polysubstituted by identical or different substituents, examples of substituents which may be mentioned being: alkyl with 1 to 4 carbon atoms, and phenyl and phenoxyalkyl with 1 to 4 carbon atoms in the alkyl part, each of which is optionally monosubstituted or polysubstituted by identical or different substituents, examples of substituents on the phenyl which may be mentioned being: halogen, alkyl with 1 to 4 carbon atoms, alkoxy and alkylthio with in each case 1 or 2 carbon atoms and halogenoalkyl, halogenoalkoxy and halogenoalkylthio with in each case 1 or 2 carbon atoms and 1 to 5 identical or different halogen atoms, such as preferably, fluorine and chlorine atoms;

R represents straight-chain or branched alkyl with 1 to 7 carbon atoms, or phenyl, phenylalkyl with 1 to 4 carbon atoms in the alkyl part, phenoxy- or phenylthio-alkyl with in each case 1 to 4 carbon atoms in the alkyl part or phenylethenyl, each of which is optionally monosustituted or polysubstituted by identical or different substituents, examples of substituents on the phenyl groups which may be mentioned being: halogen, alkyl with 1 to 4 carbon atoms, alkoxy and alkylthio with in each case 1 or 2 carbon atoms, nitro, halogenoalkyl, halogenoalkoxy and halogenoalkylthio with in each case 1 or 2 carbon atoms and 1 to 5 identical or different halogen atoms, such as, preferably, fluorine and chlorine atoms, hydroximinoalkyl with 1 to 4 carbon atoms, alkoximinoalkyl with 1 to 4 carbon atoms in each alkyl part, and phenyl, phenoxy, benzyl and benzyloxy, ach of which is optionally substituted by halogen or alkyl with 1 or 2 carbon atoms; or, preferably, R represents cycloalkyl with 5 to 7 carbon atoms, which is in each case opticnally monosubstituted or polysubstituted by identical or different alkyl radicals with 1 to 4 carbon atoms, or cycloalkyl-methyl or -ethyl with 5 to 7 carbon atoms in the cycloalkyl part, or cyclohexylethylenyl; or, preferably, R represents alkenyl with 2 to 6 carbon atoms, 2-furyl, naphthylozymethyl, 1,2,4-triazol-1-ly-methyl, 1,2,4-triazol-4-ly-methyl, imidazol-1-ly-methyl or pyrazol-1-ylmethyl;

R' represents hydrogen, alkyl which has 1 to 4 carbon atoms and is optionally substituted by phenyl, it being possible for the phenyl radical to be substituted by the substituents on phenyl mentioned under R, or alkenyl with 2 to 4 carbon atoms; and the index n represents the number 0 or 1.

Particularly preferred compounds of the formula (I) are those in which

Az represents 1,2,4-triazol-1-yl, 1,2,4-triazol-4-yl or imidazol-1-yl;

Het represents dioxolan-2-yl, 1,3-dioxan-5-yl or 1,3-dioxan-2-yl, each of which is optionally mono-, di- or tri-substituted by identical or different substituents, examples of substituents which may be mentioned being: methyl, ethyl, n-propyl, isopropyl and phenyl and phenoxymethyl, each of which is optionally mono-, di- or trisubstituted by identical or different substituents from the group comprising fluorine, chlorine, methyl, trifluoromethyl and trifluoromethoxy;

R represents tert.-butyl, trimethyl-propyl or tetramethyl-propyl, or phenyl, benzyl, phenethyl, phenoxymethyl, phenylthiomethyl or phenethenyl, each of which is optionally mono-, di- or trisubstituted by identical or different substituents, examples of substituents on the phenyl which may be mentioned being: fluorine, chlorine, methyl, trifluoromethyl, trifluoromethoxy, trifluoromethylthio, hydroximinomethyl, 1-hydroximinoethyl, methoximinomethyl and 1-methoximinoethyl, and phenyl, phenoxy, benzyl and benzyloxy, each of which is optionally substituted by chlorine and/or methyl; or R represents cyclohexyl, cyclohexylmethyl, cyclohexylethyl or cyclohexylethenyl, each of which is optionally mono- or di-substituted by identical or different substituents from the group comprising methyl, ethyl and isopropyl; or R represents allyl, dimethylpropenyl, 2-furyl, naphthyloxymethyl, 1,2,4-triazol-1-yl-methyl, 1,2,4-triazol-4-yl-methyl, imidazol-1-yl-methyl or pyrazol-1-yl-methyl;

R' represents hydrogen, methyl, 4-chlorobenzyl or allyl; and the index n represents the number 0 or 1.

Addition products of acids and those hydroxyalkyl-azolyl derivatives substituted by heterocyclic substituents, of the formula (I), in which the substituents Az, Het, R and R' and the index n have the meanings which have already been mentioned as preferred for these substituents and the index are also preferred compounds according to the invention.

Preferred acids which can be added on include hydrogen halide acids, such as, for example, hydrochloric acid and hydrobromic acid, in particular hydrochloric acid, and furthermore phosphoric acid, nitric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as, for example, p-toluenesulphonic acid and 1,5-naphthalenedisulphonic acid.

Addition products of salts of metals of main groups II to IV and of sub-groups I and II and IV to VIII and those hydroxyalkyl-azolyl derivatives substituted by heterocyclic substituents, of the formula (I), in which the substituents Het, R and R' and the index n have the meanings which have already been mentioned as preferred for these substituents and the index are also preferred compounds according to the invention.

Salts of copper, zinc, manganese, magnesium, tin, iron and nickel are particularly preferred here. Possible anions of these salts are those which are derived from acids which lead to physiologically acceptable addition products. In this connection, particularly preferred acids of this type are the hydrogen halide acids, such as, for example, hydrochloric acid and hydrobromic acid, and furthermore phosphoric acid, nitric acid and sulphuric acid.

The following compounds of the formula (Ia) may by mentioned specifically, in addition to the compounds mentioned in the preparation examples:

$$R-\underset{\underset{Az}{\overset{|}{CH_2}}}{\overset{\overset{OH}{|}}{C}}-\left(\underset{\overset{|}{CH_3}}{\overset{\overset{CH_3}{|}}{C}}\right)_n-Het \qquad (Ia)$$

| R | Az | n | Het |
|---|---|---|---|
| cyclohexyl (H) | 1,2,4-triazol-1-yl | 1 | 1,3-dioxolan-2-yl |
| 1,2,4-triazol-1-yl-CH₂— | 1,2,4-triazol-1-yl | 1 | 1,3-dioxolan-2-yl |
| 4-Cl-C₆H₄-CH=CH— | 1,2,4-triazol-1-yl | 1 | 1,3-dioxan-2-yl |
| 4-Cl-C₆H₄-CH₂-CH₂— | 1,2,4-triazol-1-yl | 1 | 1,3-dioxan-2-yl |
| 4-Cl-C₆H₄-O-CH₂— | 1,2,4-triazol-1-yl | 1 | 1,3-dioxan-2-yl |
| 4-Cl-C₆H₄-CH=CH— | 1,2,4-triazol-1-yl | 1 | 4-C₂H₅-1,3-dioxolan-2-yl |
| 4-Cl-C₆H₄-CH₂-CH₂— | 1,2,4-triazol-1-yl | 1 | 4-C₂H₅-1,3-dioxolan-2-yl |
| 4-Cl-C₆H₄-O-CH₂— | 1,2,4-triazol-1-yl | 1 | 4-C₂H₅-1,3-dioxolan-2-yl |
| 1,2,4-triazol-1-yl-CH₂— | 1,2,4-triazol-1-yl | 1 | 4-(2,4-Cl₂-C₆H₃-O-CH₂)-1,3-dioxolan-2-yl |
| 1,2,4-triazol-1-yl-CH₂— | 1,2,4-triazol-1-yl | 1 | 4-(4-Cl-C₆H₄)-1,3-dioxolan-2-yl |
| 4-Cl-C₆H₄-S-CH₂— | 1,2,4-triazol-1-yl | 1 | 1,3-dioxolan-2-yl |

-continued $$R-\underset{\underset{Az}{CH_2}}{\overset{OH}{\underset{|}{C}}}-\left(\underset{CH_3}{\overset{CH_3}{\underset{|}{\overset{|}{C}}}}\right)_n-Het \qquad (Ia)$$

| R | Az | n | Het |
|---|---|---|---|
| 4-Cl-C6H4-CH2- | 1,2,4-triazol-1-yl | 1 | 1,3-dioxolan-2-yl |
| 4-Cl-C6H4-CH2-C(CH3)2- | 1,2,4-triazol-1-yl | 1 | 1,3-dioxolan-2-yl |
| 4-Cl-C6H4-O-CH2-C(CH3)2- | 1,2,4-triazol-1-yl | 1 | 1,3-dioxolan-2-yl |
| cyclohexyl-CH=CH- | 1,2,4-triazol-1-yl | 1 | 2-ethyl-1,3-dioxolan-2-yl |
| cyclohexyl-CH2-CH2- | 1,2,4-triazol-1-yl | 1 | 2-ethyl-1,3-dioxolan-2-yl |
| (CH3)3C-C(CH3)2- | 1,2,4-triazol-1-yl | 1 | 2-(4-chlorophenoxymethyl)-1,3-dioxolan-2-yl |
| H2C=CH-C(CH3)2- | 1,2,4-triazol-1-yl | 1 | 2-(4-chlorophenoxymethyl)-1,3-dioxolan-2-yl |
| cyclohexyl-CH=CH- | 1,2,4-triazol-1-yl | 0 | 5,5-dimethyl-2-methyl-1,3-dioxan-2-yl |
| cyclohexyl-CH2-CH2- | 1,2,4-triazol-1-yl | 0 | 5,5-dimethyl-2-methyl-1,3-dioxan-2-yl |
| 2,4-Cl2-C6H3- | 1,2,4-triazol-1-yl | 1 | 2-ethyl-1,3-dioxolan-2-yl |

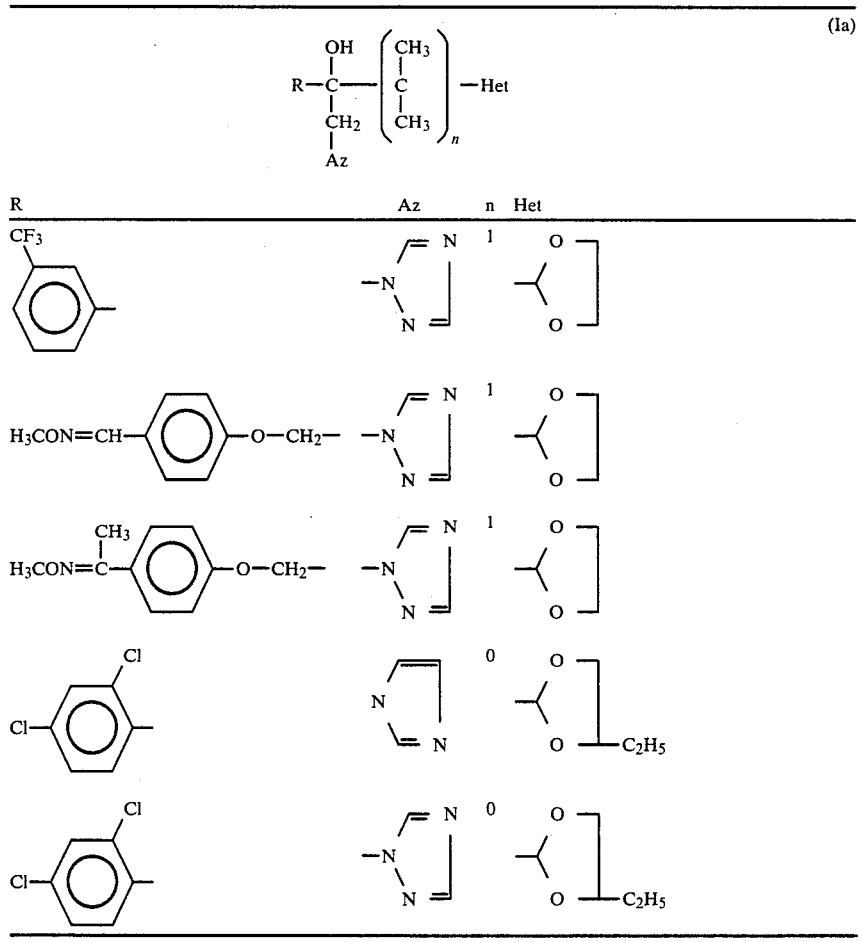

If, for example, 2-[2-(1,3-dioxolan-2-yl)-prop-2-yl]-2-(4-fluorophenoxymethyl)-oxirane and 1,2,4-triazole are used as starting substances, the course of process (a) according to the invention can be represented by the following equation:

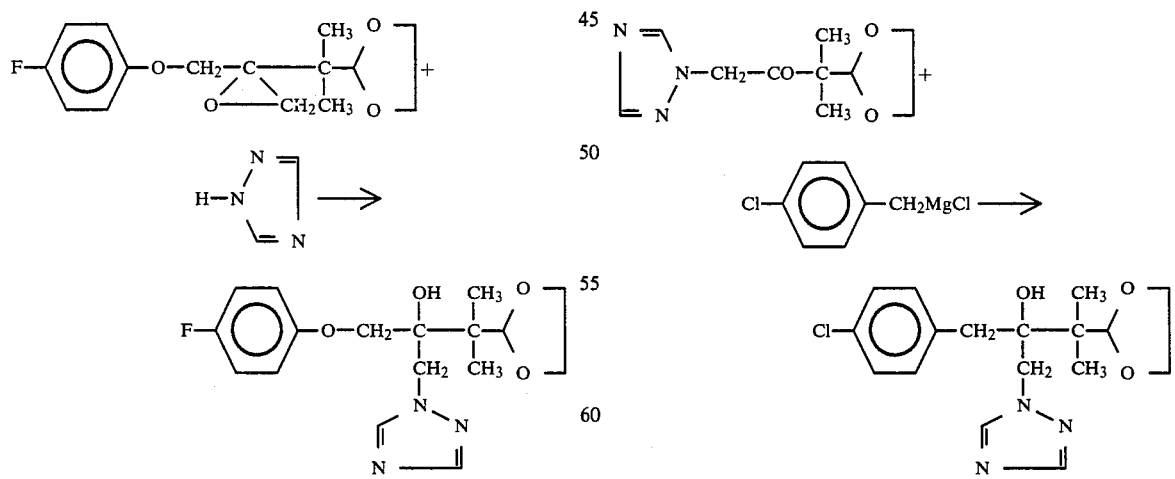

If, for example, 2-(1,3-dioxolan-2-yl)-prop-2-yl 1,2,4-triazol-1-yl-methyl ketone and 4-chlorobenzylmagnesium chloride are used as starting substances, the course of process (b) according to the invention can be represented by the following equation:

If, for example, 2-[2-(1,3-dioxolan-2-yl)-prop-2-yl]-2-(1,2,4-triazol-1-yl-methyl)-oxirane and 4-fluorophenol are used as starting substances, the course of process (c) according to the invention can be represented by the following equation:

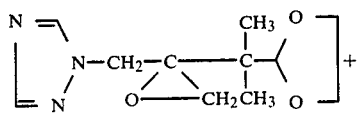

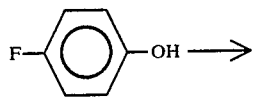

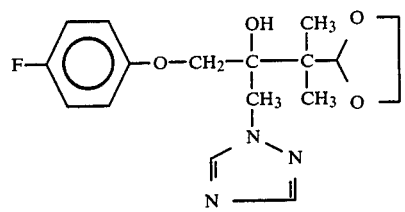

Formula (II) provides a general definition of the oxiranes to be used as starting substances for carrying out process (a) according to the invention. In this formula, Het, R and the index n preferably have the meanings which have already been mentioned as preferred for these substituents and for the index n in connection with the description of the substances of the formula (I) according to the invention.

The oxiranes of the formula (II) are not yet known. However, they can be obtained in a generally known manner, by reacting ketones of the formula (VIII)

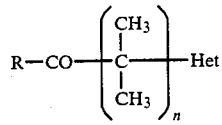

in which

Het, R and n have the abovementioned meaning, either (α) with dimethyloxosulphonium methylide of the formula (IX)

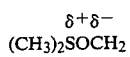
(CH₃)₂SOCH₂     (IX)

in the presence of a diluent, or (β) with trimethylsulphonium methyl-sulphate of the formula (X)

[(CH₃)₃S$^{(+)}$]CH₃SO₄$^{(-)}$     (X)

in the presence of an inert organic solvent and in the presence of a base.

The ketones of the formula (VIII), in which n = 1, required as starting substances in the preparation of the oxiranes of the formula (II) are known in some cases (compare, for example, J. Org. Chem. 32, 404 (1967)), or they are the subject of German Patent Applications No. P 32 24 130 of June 29, 1982 corresponding to U.S. Ser. No. 503,102 filed June 10, 1983 and No. P 32 24 129 of June 29, 1982 corresponding to U.S. Ser. No. 503,220 filed June 10, 1983 (now pending), or they can be obtained in a known manner, by reacting 1-(N-morpholino)-isobutene of the formula (XI)

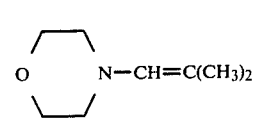

with chlorides of the formula (XII)

R—CO—Cl     (XII)

in which

R has the abovementioned meaning, in the presence of a solvent, such as, for example, diethyl ether, at temperatures between 20° C. and 120° C., and forming derivatives of the resulting keto derivatives of the formula (XIII)

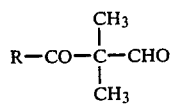

in which

R has the abovementioned meaning, on the aldehyde group with corresponding diols in the customary manner in the presence of an inert organic solvent, such as, for example, toluene, and in the presence of a strong acid, as the catalyst, such as, for example, p-toluenesulphonic acid, at temperatures between 80° C. and 110° C.

The ketones of the formula (VIII), in which n = 0, required as starting substances in the preparation of the oxiranes of the formula (II) are known in some cases (compare, for example, EP-OS [European Offenlegungsschrift] No. 0,043,923), or they can be obtained in a known manner, by reacting aldehyde-ketones (compare, for example, Houben-Weyl, Methoden der organischen Chemie [Methods of Organic Chemistry], volume 7/1. Page 185) of the formula (XIV)

R—CO—CHO     (XIV)

in which

R has the abovementioned meaning, or acetals or ketals thereof, of the formula R—C(OCH₃)₂—CHO (for their preparation compare Bull. Soc. Chim. France, 1971, page 2598) on the aldehyde group with corresponding diols in the customary manner in the presence of an inert organic solvent, such as, for example, toluene, and in the presence of a strong acid, such as, for example, p-toluenesulphonic acid, at temperatures between 40° C. and 110° C.

Ketones of the formula (VIII) in which R=optionally substituted phenethenyl or cyclohexylethenyl can also be obtained by subjecting corresponding benzaldehydes or cyclohexylcarbaldehydes to an aldol condensation with corresponding methyl ketones in the customary manner. If appropriate, the resulting ketones of the formula (VIII) in which R=optionally substituted phenethenyl or cyclohexylethenyl can be hydrogenated in the customary manner to give ketones of the formula (VIII) in which R=optionally substituted phenethyl or cyclohexylethyl (compare also the preparation examples).

The dimethyloxosulphonium methylide of the formula (IX) required in process variant (α) is known (compare J. Amer. Chem. Soc. 87, 1363–1364 (1965)). In the above reaction, it is processed in the freshly prepared state by being produced in situ by reaction of trimethlyoxosulphonium iodide with sodium hydride, sodium amide or potassium tert.-butylate in the presence of a diluent.

The trimethylsulphonium methyl-sulphate of the formula (X) required in process variant (β) is also known (compare Heterocycles 8, 397 (1977)). It is likewise employed in the above reaction in the freshly prepared state, by being produced in situ by reaction of dimethyl sulphide with dimethyl sulphate.

A possible diluent in variant (α) of the process for the preparation of the oxiranes of the formula (II) is, preferably, dimethylsulphoxide.

The reaction temperatures can be varied within a substantial range in process variant (α) described above. In general, the reaction is carried out at temperatures between 20° C. and 80° C.

The process for the preparation of the oxiranes of the formula (II) by variant (α) and the working up of the reaction mixture obtained in this synthesis are carried out by customary methods (compare J. Amer. Chem. Soc. 87, 1363-1364 (1965)).

A possible inert organic solvent in variant (β) for the prepaation of the oxiranes of the formula (II) is, preferably, acetonitrile.

Bases which can be used in process variant (β) are strong inorganic or organic bases. Sodium methylate is preferably used.

The reaction temperatures can be varied within a certain range in process variant (β) described above. In general, the reaction is carried out at temperatures between 0° C. and 60° C., preferably at room temperature.

The process for the preparation of the oxiranes of the formula (II) by variant (β) and the working up of the reaction product obtained in this synthesis are carried out by customary methods (compare Heterocycles 8, 397 (1977)).

In the process according to the invention, if appropriate, the oxiranes of the formula (II) can be further reacted directly, without isolation.

Formula (III) provides a general definition of the azoles also to be used as starting substances for process (a) according to the invention. In this formula, Az preferably has those meanings which have already been mentioned for these substituents in the definition of the invention. M preferably represents hydrogen, sodium or potassium.

The azoles of the formula (III) are generally known compounds of organic chemistry.

Formula (IV) provides a general definition of the azolo-ketones to be used as starting substances in carrying out process (b) according to the invention. In this formula Az, Het and the index n preferably have the meanings which have already been mentioned as preferred for these substituents or for the index n in connection with the description of the substances of the formula (I) according to the invention.

Some of the azolo-ketones of the formula (IV) are known (compare, for example, EP-OS [European Published Specification ] No. 0,043,923), but some of them are the subject of U.S. Ser. No. 503,200 filed June 10, 1983, now pending. The azolo-ketones of the formula (IV) can be obtained in a generally known manner, by reacting halogenomethyl ketones of the formula (XV)

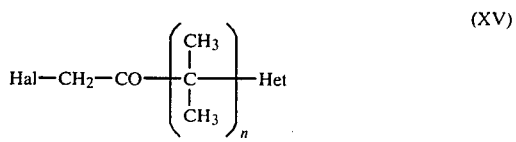

in which

Het and n have the abovementioned meaning and

Hal represents chlorine or bromine, with 1,2,4-triazole or imidazole in the presence of an inert organic solvent, such as, for example, acetone, and in the presence of an acid-binding agent, such as, for example, potassium carbonate, at temperatures between 20° C. and 150° C. in the customary manner. The halogenomethyl ketones of the formula (XV) in which n=1 which are required as starting substances in the preparation of the azolo-ketones of the formula (IV) are not yet known; they are also the subject of U.S. Ser. No. 503,200 filed June 10, 1983, now pending. They can be obtained by the preparation described above for the ketones of the formula (VIII) in which n is 1.

Some of the halogenomethyl ketones of the formula (XV) in which n=0 equired as stating substances in the preparation of the azolo-ketones of the formula (IV) are known (compare, for example, EP-OS ]European Published Specification] No. 0,043,923); they can be obtained in a known manner by halogenation, such as, for example, with N-bromosuccinamide, of corresponding ketones of the formula (VIII).

Formula (V) provides a general definition of the organomagnesium compounds also to be used as starting substances for process (b) according to the invention. In this formula, R preferably has the meanings which have already been mentioned for this substituent in connection with the description of the substances of the formula (I) according to the invention.

The organomagnesium compounds of the formula (V) are generally known compounds of organic chemistry (so-called "Grignard" compounds); or they are obtained in a generally known manner.

Formula (VI) provides a general definition of the azolo-oxiranes to be used as starting substances in carrying out process (c) according to the invention. In this formula, Az, Het and the index n preferably have the meanings which have already been mentioned as preferred for these substituents and for the index n in connection with the description of the substances of the formula (I) according to the invention.

The azolo-oxiranes of the formula (VI) are not yet known; however, they can be obtained in a generally known manner by epoxidizing azolo-ketones of the formula (IV) in accordance with the abovementioned process variants (60 ) and (β).

The phenols and thiophenols also used as starting substances for process (c) according to the invention are given by the preferred definition of the radical R in the substances of the formula (I) according to the invention.

Formula (VII) provides a general definition of the organometallic compounds also to be used as starting substances for process (c) according to the invention. In this formula, R preferably has the meanings which have already been mentioned for this substituent in connection with the description of the substances of the formula (I) according to the invention. Me preferably represents lithium, sodium, potassium or the grouping —Mg—X, in which X represents chlorine, bromine or iodine.

The phenols and thiophenols and the organometallic compounds of the formula (VII) are generally known compounds of organic chemistry.

Possible diluents for process (a) according to the invention are organic solvents which are inert under the reaction conditions. Preferred solvents include alcohols, such as, for example, ethanol, methoxyethanol or propanol; ketones, such as, for example, 2-butanone; nitriles, such as, for example, acetonitrile; esters, such as, for example, ethyl acetate; ethers, such as, for example, dioxane; aromatic hydrocarbons, such as, for example, benzene and toluene; and amides, such as, for example, dimethylformamide.

Possible bases for process (a) according to the invention are all the inorganic and organic bases which can customarily be used. Preferred bases include alkali metal carbonates, such as, for example, sodium and potassium carbonate; alkali metal hydroxides, such as, for example, sodium hydroxide; alkali metal alcoholates, such as, for example, sodium and potassium methylate and ethylate; alkali metal hydrides, such as, for example, sodium hydride; and lower tertiary alylamines, cycloalkylamines and aralkylamines, such as, in particular, triethylamine.

The reaction temperatures can be varied within a substantial range in carrying out process (a) according to the invention. In general, the reaction is carried out at temperatures between 0° C. and 200° C., preferably between 60° C. and 150° C.

In carrying out process (a) according to the invention, 1 to 2 mols of azole and, if appropriate, 1 to 2 mols of base are preferably employed per mol of oxirane of the formula (II). The end products are isolated in the generally customary manner.

Possible diluents for process (b) according to the invention are all the solvents customary for a Grignard reaction. Preferred solvents include ethers, such as diethyl ether or tetrahydrofuran, and mixtures with other organic solvents, such as, for example, benzene.

The reaction temperatures can be varied within a substantial range in carrying out process (b) according to the invention. In general, the reaction is carried out between about 20° C. and 120° C., preferably between about 30° C. and about 80° C.

In carrying out process (b), an excess of 3 to 5 mols of an organometallic compound of the formula (V) is preferably employed per mol of azolo-ketone of the formula (IV). The end products are isolated in the generally customary manner.

Possible diluents for process (c) according to the invention are organic solvents which are inert under the reaction conditions. Preferred solvents include alcohols, such as, for example, ethanol, methoxyethanol or propanol; ketones, such as, for example, 2-butanone; nitriles, such as, for example, acetonitrile; esters, such as, for example, ethyl acetate; ethers, such as, for example, dioxane; aromatic hydrocarbons, such as, for example, benzene and toluene; and amides, such as, for example, dimethylformamide.

Possible bases for process (c) according to the invention are all the inorganic and organic bases which can customarily be used. Preferred bases include the compounds which have already been mentioned for process (a).

The reaction temperatures can be varied within a substantial range in carrying out process (c) according to the invention. In general, the reaction is carried out at temperatures between 0° C. and 200° C., preferably between 60°0 C. and 150° C.

In carrying out process (c) according to the invention, 1 to 2 mols of (thio)phenol and, if appropriate, 1 to 2 mols of base, and 1 to 3 mols of the organometallic compounds of the formula (VII) are employed per mol of azolo-oxirane of the formula (VI). The end products are in each case isolated in the generally customary manner.

The preparation of the ether compounds of the formula (I) by process (d) according to the invention is advantageously carried out by converting compounds of the formula (I) into the alkali metal alcoholate by means of an alkali metal hydride or amide in a suitable inert organic solvent, and reacting the alcoholate immediately, without isolation, with a corresponding halide, such as, in particular, an alkyl halide, in a temperature range between 0° and 80° C., the ethers of the compounds of the formula (I) being obtained in one operation, with elimination of alkali metal halide.

In a preferred embodiment, the preparation of the alcoholates and further reaction thereof with a halide are advantageously carried out in a two-phase system, such as, for example, aqueous sodium hydroxide solution or potassium hydroxide solution/toluene or methylene chloride, with addition of 0.01 to 1 mol of a phase transfer catalyst, such as, for example, ammonium or phosphonium compounds, the alcoholates being formed in the organic phase or at the phase boundary and reacting with the halides in the organic phase.

The hydroxy compounds (in which, in formula (I), R' represents hydrogen) obtainable by processes (a), (b) and (c) according to the invention can also be converted into the corresponding esters.

The compounds are thus interesting intermediates.

The preparation of the esters is advantageously carried out by reacting the hydroxy compounds with, for example, acid halides in the presence of an inert organic solvent, such as, for example, ethyl acetate, at temperatures between 0° C. and 100° C.; or reacting the hydroxy compounds with acid anhydrides in the presence of an inert organic solvent, such as, for example, methylene chloride or an excess of acid anhydride, and in the presence of a catalyst, such as, for example, sodium acetate, at temperatures between 0° C. and 150° C.

The compounds of the formula (I) can also be converted into acid addition salts or metal salt complexes.

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and if appropriate purified by washing with an inert organic solvent.

The metal complexes of compounds of the formula (I) can be obtained in a simple manner by customary processes, thus, for example by dissolving the metal salts in alcohol, for example ethanol, and adding the solution to the compound of the formula (I). The metal salt complexes can be purified in a known manner, for example by filtration, isolation and, if necessary, by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating Puccinia species, such as against the brown rust of wheat causative organism (*Puccinia recondita*), and Botrytis species, such as against grey mold (*Botrytis cinerea*), and also for combating mildew, *Leptosphaeria nodorum, Cochliobolus sativus* and *Pyrenophora teres* on cereals, and against Pyricularia and Pellicularia on rice.

When used in appropriate amounts, the substances according to the invention also exhibit a growth-regulating action.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant those liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.2%, are required at the place of action.

Preparation Examples

EXAMPLE 1

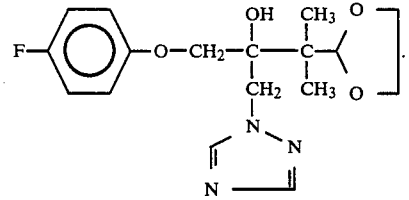

(Process a)

A solution of 17.6 g (0.0623 mol) of 2-[2-(1,3-dioxolan-2-yl)-prop-2-yl]-2-(4-fluorophenoxymethyl)-oxirane in 30 ml of n-propanol are added dropwise to a solution of 4.93 g (0.0715 mol) of 1,2,4-triazole and 0.36 g (0.0065 mol) of potassium hydroxide in 30 ml of n-propanol at room temperature. The reaction mixture is heated under reflux for 2 days and is then concentrated. The residue is taken up in ethyl acetate and the mixture is washed twice with water and once with saturated sodium chloride solution, dried over sodium sulphate and concentrated. The residue is purified by column chromatography (dichloromethane/ethyl acetate=3:1) and recrystallized from a little ether.

10.2 g (47% of theory) of 3-(1,3-dioxolan-2-yl)-1-(4-fluorophenoxy)-3-methyl-2-(1,2,4-triazol-1-yl-methyl)-2-butanol of melting point 102° C. to 104° C. are obtained.

Preparation of the starting substance:

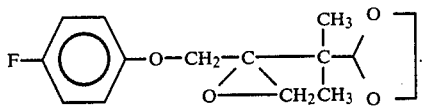

8.4 g (0.0748 mol) of potassium tert.-butylate are added to a suspension of 16.47 g (0.0748 mol) of trimethylsulphoxonium iodide in 20 ml of absolute dimethylsulphoxide at room temperature. The mixture is subsequently stirred for 30 minutes and a solution of 3-(1,3-dioxolan-2-yl)-1-(4-fluorophenoxy)-3-methyl-2-butanone in 20 ml of absolute toluene is then added dropwise. The reaction mixture is stirred overnight at room temperature and is then heated at 50° C. for 2 hours and cooled, and water and toluene are added. The toluene phase is separated off, washed twice with water and once with saturated sodium chloride solution, dried over sodium sulphate and concentrated.

17.6 g (91% of theory) of 2-[2-(1,3-dioxolan-2-yl)-prop-2-yl]-2-(4-fluorophenoxymethyl)-oxirane are obtained as an oil, which is further reacted directly.

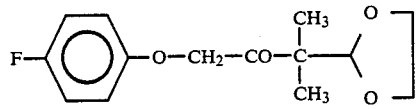

A mixture of 16.7 g (0.15 mol) of 4-fluorophenol, 29 g (0.15 mol) of 1-chloro-3-(1,3-dioxolan-2-yl)-3-methyl-2-butanone and 23.4 g (0.17 mol) of powdered potassium carbonate in 300 ml of methyl ethyl ketone is heated under reflux for 16 hours. It is allowed to cool and is filtered. The filtrate is concentrated, the residue is taken up in dichloromethane, the mixture is washed once with 5% strength sodium hydroxide solution and once with water, dried over sodium sulphate and concentrated and the residue is distilled. 29 g (72% of theory) of 3-(1,3-dioxolan-2-yl)-1-(4-fluorophenoxy)-3-methyl-2-butanone of boiling point 143° C. to 145° C./0.1 mbar are obtained.

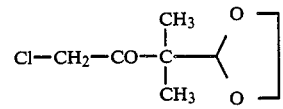

204 g (1.38 mols) of 4-chloro-2,2-dimethyl-3-ketobutanal are heated with 93 g (1.5 mols) of ethylene glycol and 0.7 g of p-toluenesulphonic acid in 400 ml of methylene chloride for 3 hours, using a water separator. The organic phase is extracted with 150 ml of 5% strength sodium hydroxide solution and then 400 ml of water. The solvent is distilled off and the residue is distilled under a water pump vacuum.

211 g (79.8% of theory) of 1-chloro-3-(dioxolan-2-yl-3-methyl-2-butanone of boiling point 127° C. to 128° C./14 mbar are obtained.

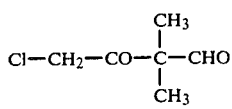

210 g (1.5 mols) of 1-(N-morpholino)-isobutene are added dropwise, at 5° C., to 169 g (1.5 mols) of chloroacetyl chloride dissolved in 350 ml of diethyl ether, in the course of one hour. When the addition has ended, the mixture is stirred for a further 3 hours, while cooling under reflux. The solution is poured onto 100 g of ice, the pH is brought to 5 with aqueous sodium bicarbonate solution and the ether phase is separated off. The aqueous phase is extracted with 100 ml of diethyl ether, the organic phases are combined and dried over sodium sulphate, the solvent is distilled off and the residue is distilled under a water pump vacuum.

136.4 g (61% of theory) of 4-chloro-2,2-dimethyl-3-keto-butanal of boiling point 95° C. to 98° C./14 mbar are obtained.

EXAMPLE 2 AND 3

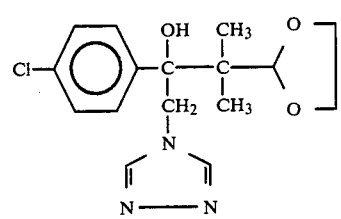
(Example 2)

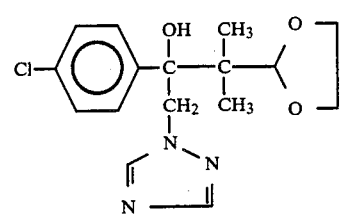
(Example 3)

(Process a)

A solution of 26.8 g (0.1 mol) of 2-(4-chlorophenyl)-2-[2-(1,3-dioxolan-2-yl)-prop-2-yl]-oxirane, 7.6 g (0.11 mol) of 1,2,4-triazole and 0.5 g of potassium hydroxide in 200 ml of absolute butanol is heated under reflux for 18 hours. The mixture is allowed to cool to room temperature, and 800 ml of water are added. The organic phase is separated off, dried over sodium sulphate and concentrated. The residue is stirred with 200 ml of isopropyl ether/ethyl acetate (10:1).

The solid which precipitates is filtered off and dried. 4.5 g (13.3% of theory) of 3-(1,3-dioxolan-2-yl)-2-(4-chlorophenyl)-3-methyl-1-(1,2,4-triazol-4-yl)-2-butanol (Example 2) of melting point 180° C. to 182° C. are obtained.

The filtrate is concentrated and the residue is first taken up in 350 ml of acetone, and 8 g of 1,5-naphthalenedisulphonic acid in 30 ml of acetone are then added. The mixture is stirred at 0° C. for 6 hours, the solid is filtered off with suction and saturated, aqueous sodium bicarbonate/methylene chloride solution is added. The organic phase is separated off, dried over sodium sulphate and concentrated.

19 g (56.2% of theory) of 3-(1,3-dioxolan-2-yl)-2-(4-chlorophenyl)-3-methyl-1-(1,2,4-triazol-1-yl)-2-butanol (Example 3) are obtained as an oil.

Preparation of the starting substance:

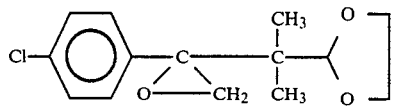

29.5 g (0.208 mol) of methyl iodide are added dropwise to 13.7 g (0.22 mol) of dimethyl sulphide in 130 ml of absolute dimethylsulphoxide and 120 ml of absolute tetrahydrofuran, whereupon the temperature rises to about 30° C. The mixture is subsequently stirred for 5 hours and a solution of 33 g (0.13 mol) of 4-chlorophenyl 2-[2-(1,3-dioxolan-2-yl)-prop-2-yl]ketone in 100 ml of absolute toluene is then added. 9.5 g of sodium methylate are then added in portions in the course of one hour. The reaction mixture is subsequently stirred for 3 hours and a further 5.6 g of sodium methylate are added in two portions in the course of 30 minutes. The reaction mixture is stirred overnight and poured onto 700 ml of ice-water. The organic phase is separated off and the aqueous phase is extracted by shaking with 200 ml of toluene. The combined organic phases are washed with two 1,000 ml portions of water, dried over sodium sulphate and concentrated. The oily residue is degassed in vacuo.

26.8 g of 2-(4-chlorophenyl)-2-[2-(1,3-dioxolan-2-yl)-prop-2-yl]-oxirane are obtained as an oil, which is further reacted directly.

EXAMPLE 4

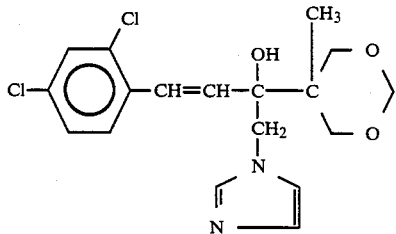

(Process a)

13.6 g (0.2 mol) of imidazole are added in portions to 6 g of sodium hydride (80% strength, 0.2 mol) in 200 ml of absolute dimethylformamide, whereupon the temperature rises to about 45° C. The mixture is subsequently stirred for 30 minutes and 34 g (0.108 mol) of 2-(2,4-dichlorophenethenyl)-2-(5-methyl-1,3-dioxan-5-yl)-oxirane in 50 ml of absolute dimethylformamide are then added. The reaction mixture is stirred at 80° C. for 4 hours. It is allowed to cool and is poured onto 800 ml of ice-water/600 ml of methylene chloride. The mixture is subsequently stirred for 45 minutes and the methylene chloride phase is separated off, washed twice with water, dried over sodium sulphate and concentrated. The residue is recrystallized from ether.

10.5 g (25.4% of theory) of 1-(2,4-dichlorophenyl)-4-(imidazol-1-yl)-3-(5-methyl-1,3-dioxan-5-yl)-1-buten-3-ol of melting point 142° C. to 144° C. are obtained.

Preparation of the starting substance:

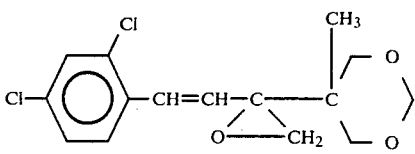

56.8 g (0.4 mol) of methyl iodide are added dropwise to 26.4 g (0.425 mol) of dimethyl sulphide in 180 ml of absolute dimethylsulphoxide and 175 ml of absolute tetrahydrofuran, whereupon the temperature rises to about 35° C. The mixture is subsequently stirred for 16 hours and a solution of 75.2 g (0.25 mol) of 2,4-dichlorophenethenyl 5-methyl-1,3-dioxan-5-yl ketone in 200 ml of absolute toluene is then added. 17.4 g (0.3 mol) of sodium methylate are introduced in portions at 0° C. The mixture is subsequently stirred for 3 hours, a further 10.8 g (0.2 mol) of sodium methylate are added and the mixture is stirred overnight. 250 ml of water are added to the reaction mixture, the toluene phase is separated off and the aqueous phase is extracted with two 150 ml portions of toluene. The combined toluene phases are washed with three 700 ml portions of water, dried over sodium sulphate and concentrated. The oily residue is degassed in vacuo.

69 g of 2-(2,4-dichlorophenethenyl)-2-(5-methyl-1,3-dioxan-5-yl)-oxirane are obtained as an oil, which is further reacted directly.

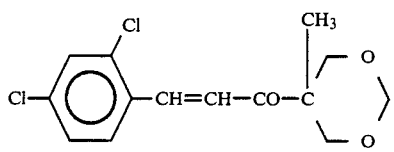

35 ml of 10% strength sodium hydroxide solution are added dropwise to 70 g (0.4 mol) of 2,4-dichlorobenzaldehyde and 57.5 g of methyl 5-methyl-1,3-dioxan-5-yl) ketone (85% strength, 0.4 mol) in 140 ml of ethanol and 0 ml of water. The reaction mixture is subsequently stirred at room temperature for 8 hours and is then poured onto 400 ml of methylene chloride. The organic phase is separated off, washed with water, dried over sodium sulphate and concentrated. The oily residue crystallizes after trituration with ether.

80 g of 2,4-dichlorophenethenyl 5-methyl-1,3-dioxan-5-yl ketone of melting point 100° C. to 102° C. are obtained.

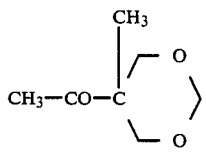

360 g (5 mols) of methyl ethyl ketone and 225 g (2.5 mols) of trioxane are heated under reflux in 1,000 ml of chloroform, with addition of 40 ml of concentrated sulphuric acid, for 2 hours. The mixture is allowed to cool, 2 liters of water are added and the mixture is subsequently stirred for 10 minutes. The organic phase is separated off and stirred into saturated, aqueous sodium bicarbonate solution and the mixture is again subsequently stirred for 10 minutes. The organic phase is separated off, dried over sodium sulphate and concentrated. The residue is distilled in vacuo.

199 g of methyl 5-methyl-1,3-dioxan-5-yl ketone of boiling point 50° C. to 52° C./0.08 mbar are obtained.

EXAMPLE 5

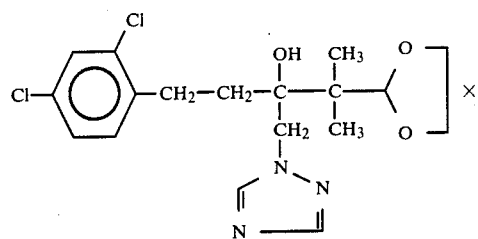

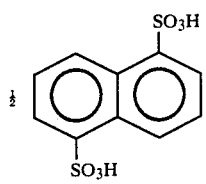

(Process a / salt formation)

13.8 g (0.2 mol) of 1,2,4-triazole are added in portions to a suspension of 6 g of sodium hydride (80% strength, 0.2 mol) in 330 ml of absolute dimethylformamide. The mixture is subsequently stirred for 30 minutes and 45 g (0.136 mol) 2-(2,4-dichlorophenylethyl)-2-[2-(13-dioxolan-2-yl)-pro-2-yl]-oxirane in 80 ml of dimethylforamide is then added. The reaction mixture is stirred at 80° C. for 4 hours. It is then allowed to cool and is poured onto 600 ml of ice-water/800 ml of methylene chloride. The methylene chloride phase is separated off, washed with two 1,500 ml portions of water, dried over sodium sulphate and concentrated. The oily residue is taken up in 400 ml of acetone, and 14.4 g of 1,5-naphthalenedisulphonic acid in 40 ml of acetone are added at 0° C. The mixture is subsequently stirred for 5 hours and the precipitate formed is filtered off with suction.

43.1 g (29.1% of theory) of 1-(2,4-dichlorophenyl)-4-(1,3-dioxolan-2-yl)-4-methyl-3-(1,2,4-triazol-1-yl-methyl)-3-pentanol 1,5-naphthalenedisulphonate of melting point 183° C. are obtained.

Preparation of the starting substance:

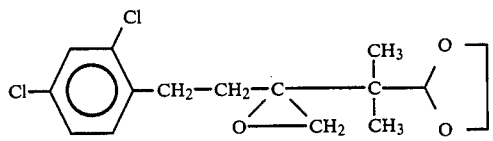

90 g of 2-(2,4-dichlorophenylethyl)-2-[2-(1,3-dioxolan-2-yl)-prop-2-yl]-oxirane are obtained as an oil, is further reacted directly, by reaction of 83 g (0.262 mol) of 2,4-dichlorophenylethyl 2-(1,3-dioxolan-2-yl)-prop-2-yl ketone with 28.2 g (0.455 mol) of dimethylsulphide/60 g of methyl iodide according to Example 3.

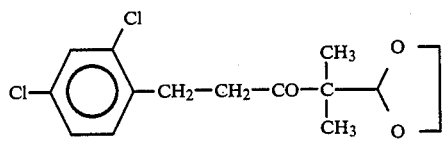

100 g of 2,4-dichlorophenylethenyl 2-(1,3-dioxolan-2-yl)-pro-2-yl) ketone are heated to 25° C. under a pressure of 55 bar with 10 g of Raney nickel in 600 ml of tetrahydrofuran for 25 minutes. The reaction mixture is then concentrated and the residue is distilled in vacuo.

83 g of 2,4-dichlorophenylethyl 2-(1,3-dioxolan-2-yl)-prop-2-yl ketone of boiling point 148° C./0.1 mbar are obtained.

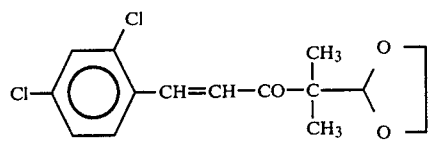

95 ml of 10% strength sodium hydroxide solution are added dropwise to 196 g (1.12 mol) of 2,4-dichlorobenzaldehyde and 178 g (1.125 mol) of methyl 2-(1,3-dioxolan-2-yl)-prop-2-yl ketone in 400 ml of ethanol and 140 ml of water. The reaction mixture is subsequently stirred for 10 hours and the solid formed is filtered off with suction and washed with ethanol.

309 g of 2,4-dichlorophenylethenyl 2-(1,3-dioxolan-2-yl)-pro-2-yl ketone of melting point 92° C. to 93° C. are obtained.

EXAMPLE 6:

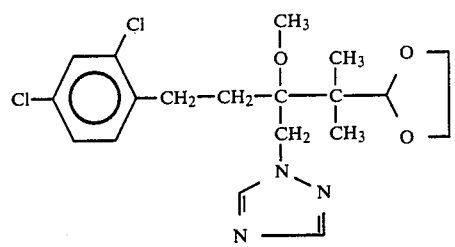

(Process d / ether formation)

1.4 g (0.046 mol) of sodium hydride are added to 18 g (0.045 mol) of 1-(2,4-dichlorophenyl)-4-(1,3-dioxan-2-yl)-4-methyl-3-(1,2,4-triazol-1-yl-methyl)-3-pentanol in 150 ml of absolute dioxane. The mixture is subsequently stirred at room temperature for 5 hours and 7.1 g (0.05 mol) of methyl iodide are added. The mixture is then stirred overnight, and 0.7 g (0.023 mol) of sodium hydride and 3.5 g (0.025 mol) of methyl iodide are again added. After subsequently stirring for a further period, the inorganic salts are filtered off with suction. The filtrate is concentrated, the oily residue is taken up in methylene chloride and the mixture is rinsed with two 600 ml portions of water, dried over sodium sulphate and concentrated. The residue is recrystallized from isopropyl ether.

12 g (64.4% of theory) of 1-(2,4-dichlorophenyl)-4-(1,3-dioxan-2-yl)-3-methoxy-4-methyl-3-(1,2,4-triazol-1-yl-methyl)-pentane of melting point 130° C. to 132° C. are obtained.

The following compounds of the general formula (Ia) are obtained in an analogous manner and by the process descriptions according to the invention:

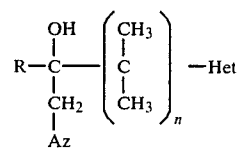

| Example No. | R | Az | n | Het | Melting point (°C.) or $n_D^{20}$ |
|---|---|---|---|---|---|
| 7 | 4-Cl-C6H4-CH2-CH2- | 1,2,4-triazol-1-yl | 1 | 1,3-dioxolan-2-yl | 179 (× ½ NDS) |
| 8 | 2,4-Cl2-C6H3-CH2-CH2- | 1,2,4-triazol-1-yl | 0 | 5-methyl-1,3-dioxan-5-yl | 119–121 |
| 9 | 2,4-Cl2-C6H3-CH2-CH2- | 1,2,4-triazol-1-yl | 0 | 5-methyl-1,3-dioxan-5-yl | 125–127 |
| 10 | 4-Cl-C6H4-CH=CH- | 1,2,4-triazol-1-yl | 1 | 1,3-dioxolan-2-yl | 116–118 |
| 11 | 2,4-Cl2-C6H3-CH=CH- | 1,2,4-triazol-1-yl | 1 | 1,3-dioxolan-2-yl | 93 |
| 12 | 4-Cl-C6H4-CH=CH- | 1,2,4-triazol-1-yl | 0 | 5-methyl-1,3-dioxan-5-yl | 182–184 |
| 13 | 2,4-Cl2-C6H3-CH=CH- | 1,2,4-triazol-1-yl | 0 | 5-methyl-1,3-dioxan-5-yl | 171–173 |
| 14 | 4-C6H5-C6H4-O-CH2- | 1,2,4-triazol-1-yl | 1 | 1,3-dioxolan-2-yl | 106–107 |
| 15 | 4-Cl-C6H4-O-CH2- | 1,2,4-triazol-1-yl | 1 | 1,3-dioxolan-2-yl | 105–107 |
| 16 | 4-Cl-C6H4-O-CH2- | 1,2,4-triazol-1-yl | 0 | 5-methyl-1,3-dioxan-5-yl | 102–107 |
| 17 | 2,4-Cl2-C6H3-O-CH2- | 1,2,4-triazol-1-yl | 0 | 5-methyl-1,3-dioxan-5-yl | 117–122 |

-continued

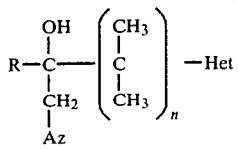
(Ia)

| Example No. | R | Az | n | Het | Melting point (°C.) or $n_D^{20}$ |
|---|---|---|---|---|---|
| 18 | 4-Cl-C₆H₄-O-CH₂- | 1,2,4-triazol-1-yl | 0 | CH₃, 1,3-dioxan-2-yl | 220–225 |
| 19 | 4-Cl-C₆H₄-CH₂-CH₂- | imidazol-1-yl | 1 | 1,3-dioxolan-2-yl | 93 |
| 20 | 2,4-Cl₂-C₆H₃-CH₂-CH₂- | imidazol-1-yl | 1 | 1,3-dioxolan-2-yl | 140–143 (× ½ NDS) |
| 21 | 2,4-Cl₂-C₆H₃-CH₂-CH₂- | imidazol-1-yl | 0 | CH₃, 1,3-dioxan-2-yl | 122–124 |
| 22 | 4-Cl-C₆H₄-CH₂-CH₂- | imidazol-1-yl | 0 | CH₃, 1,3-dioxan-2-yl | 68–73 |
| 23 | 4-Cl-C₆H₄-CH=CH- | imidazol-1-yl | 1 | 1,3-dioxolan-2-yl | 164–166 |
| 24 | 2,4-Cl₂-C₆H₃-CH=CH- | imidazol-1-yl | 1 | 1,3-dioxolan-2-yl | 122–125 |
| 25 | 4-Cl-C₆H₄-CH=CH- | imidazol-1-yl | 0 | CH₃, 1,3-dioxan-2-yl | 192–195 |
| 26 | 4-Cl-C₆H₄-O-CH₂- | imidazol-1-yl | 0 | CH₃, 1,3-dioxan-2-yl | 141–144 |
| 27 | 2,4-Cl₂-C₆H₃-O-CH₂- | imidazol-1-yl | 0 | CH₃, 1,3-dioxan-2-yl | 176–177 |

-continued

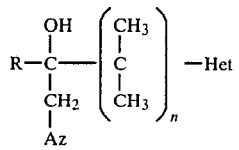
(Ia)

| Example No. | R | Az | n | Het | Melting point (°C.) or $n_D^{20}$ |
|---|---|---|---|---|---|
| 28 | (triazolyl-N-CH2—) | 1,2,4-triazol-1-yl | 1 | 1,3-dioxolane | 1,5240 |
| 29 | biphenyl-O-CH2— | imidazol-1-yl | 1 | 2-ethyl-1,3-dioxolane | 89–92 |
| 30 | 4-Cl-C6H4-O-CH2— | imidazol-1-yl | 1 | 1,3-dioxane | 129–30 |
| 31 | biphenyl-O-CH2— | imidazol-1-yl | 1 | 1,3-dioxane | 138–39 |
| 32 | biphenyl-O-CH2— | 1,2,4-triazol-1-yl | 1 | 1,3-dioxane | 149 |
| 33 | 4-Cl-C6H4-CH=CH— | 1,2,4-triazol-1-yl | 1 | 1,3-dioxane | 147–49 |
| 34 | 4-Cl-C6H4-CH=CH— | imidazol-1-yl | 1 | 1,3-dioxane | 152–55 |
| 35 | 4-Cl-C6H4-CH2-CH2— | imidazol-1-yl | 1 | 2-ethyl-1,3-dioxolane | viscous oil |
| 36 | 4-Cl-C6H4-CH2-CH2— | 1,2,4-triazol-1-yl | 1 | 2-ethyl-1,3-dioxolane | viscous oil |
| 37 | 4-Cl-C6H4-O-CH2— | 1,2,4-triazol-1-yl | 1 | 2-ethyl-1,3-dioxolane | 169–72 (× ½ NDS) |

-continued

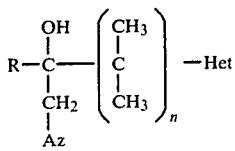
(Ia)

| Example No. | R | Az | n | Het | Melting point (°C.) or $n_D^{20}$ |
|---|---|---|---|---|---|
| 38 | 4-Cl-C₆H₄-O-CH₂- | imidazol-1-yl | 1 | 2-ethyl-1,3-dioxolan-2-yl | viscous oil |
| 39 | 4-Cl-C₆H₄-O-CH₂- | 1,2,4-triazol-1-yl | 1 | 1,3-dioxan-2-yl | viscous oil |
| 40 | 4-Cl-C₆H₄-CH₂-CH₂- | 1,2,4-triazol-1-yl | 1 | 1,3-dioxan-2-yl | 110–12 |
| 41 | 4-Cl-C₆H₄-CH₂-CH₂- | 1,2,4-triazol-1-yl | 1 | 1,3-dioxan-2-yl | 117–19 |
| 42 | 1,2,4-triazol-1-yl-CH₂- | 1,2,4-triazol-1-yl | 1 | 2-(2,5-dichlorophenoxymethyl)-1,3-dioxolan-2-yl | 1.5461 |
| 43 | 4-Cl-C₆H₄-CH=CH- | 1,2,4-triazol-1-yl | 1 | 2-ethyl-1,3-dioxolan-2-yl | 80 |
| 44 | 4-Cl-C₆H₄-CH=CH- | imidazol-1-yl | 1 | 2-ethyl-1,3-dioxolan-2-yl | 88–90 |
| 45 | 4-Cl-C₆H₄-S-CH₂- | 1,2,4-triazol-1-yl | 1 | 1,3-dioxolan-2-yl | viscous oil |
| 46 | 4-biphenyl-O-CH₂- | 1,2,4-triazol-1-yl | 1 | 2-ethyl-1,3-dioxolan-2-yl | 105 |

-continued

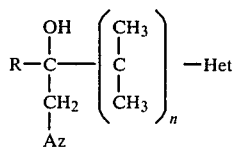
(Ia)

| Example No. | R | Az | n | Het | Melting point (°C.) or $n_D^{20}$ |
|---|---|---|---|---|---|
| 47 | 2,4-Cl₂-C₆H₃-CH=CH- | imidazol-1-yl | 0 | 2,2-dimethyl-1,3-dioxan-5-yl (with CH₃ groups) | viscous oil |
| 48 | 2,4-Cl₂-C₆H₃-CH=CH- | 1,2,4-triazol-1-yl | 0 | 2,2-dimethyl-1,3-dioxan-5-yl (with CH₃ groups) | viscous oil |
| 49 | furan-2-yl | 1,2,4-triazol-1-yl | 1 | 1,3-dioxolan-2-yl | viscous oil |
| 50 | furan-2-yl | 1,2,4-triazol-1-yl | 1 | 1,3-dioxolan-2-yl | 100 |
| 51 | 4-Cl-C₆H₄-CH₂-CH₂- | 1,2,4-triazol-1-yl | 1 | 2-propyl-1,3-dioxolan-2-yl | viscous oil |
| 52 | 2,4-Cl₂-C₆H₃-CH₂CH₂- | imidazol-1-yl | 1 | 2-propyl-1,3-dioxolan-2-yl | 115 |
| 53 | 2,4-Cl₂-C₆H₃-CH₂CH₂- | 1,2,4-triazol-1-yl | 1 | 2-propyl-1,3-dioxolan-2-yl | viscous oil |
| 54 | 4-Cl-C₆H₄-CH₂CH₂- | imidazol-1-yl | 1 | 2-methyl-1,3-dioxolan-2-yl | viscous oil |
| 55 | 2,4-Cl₂-C₆H₃-CH₂CH₂- | imidazol-1-yl | 1 | 2-methyl-1,3-dioxolan-2-yl | viscous oil |

-continued $$\underset{Az}{\overset{OH}{\underset{CH_2}{R-C-}}}\left(\underset{CH_3}{\overset{CH_3}{\underset{|}{C}}}\right)_n-Het \quad (Ia)$$

| Example No. | R | Az | n | Het | Melting point (°C.) or $n_D^{20}$ |
|---|---|---|---|---|---|
| 56 | 3-CH₃, 4-Cl-C₆H₃-O-CH₂- | imidazol-1-yl | 1 | 4-methyl-1,3-dioxolan-2-yl | viscous oil |
| 57 | 3-CH₃, 4-Cl-C₆H₃-O-CH₂- | imidazol-1-yl | 1 | 1,3-dioxolan-2-yl | 123 |
| 58 | 3-CH₃, 4-Cl-C₆H₃-O-CH₂- | 1,2,4-triazol-1-yl | 1 | 1,3-dioxolan-2-yl | 81 |
| 59 | biphenyl-CH=CH- | imidazol-1-yl | 1 | 5-methyl-1,3-dioxan-2-yl | 146 |
| 60 | biphenyl-CH=CH- | 1,2,4-triazol-1-yl | 1 | 5-methyl-1,3-dioxan-2-yl | 170 |
| 61 | biphenyl-CH₂CH₂- | 1,2,4-triazol-1-yl | 0 | 5-methyl-1,3-dioxan-2-yl | 98 |
| 62 | biphenyl-CH₂CH₂- | imidazol-1-yl | 0 | 5-methyl-1,3-dioxan-2-yl | 131 |
| 63 | 3-CH₃, 4-Cl-C₆H₃-O-CH₂- | 1,2,4-triazol-1-yl | 1 | 4-methyl-1,3-dioxolan-2-yl | viscous oil |
| 64 | 3-CH₃, 4-Cl-C₆H₃-O-CH₂- | imidazol-1-yl | 1 | 4-ethyl-1,3-dioxolan-2-yl | viscous oil |
| 65 | 3-CH₃, 4-Cl-C₆H₃-O-CH₂- | 1,2,4-triazol-1-yl | 1 | 4-ethyl-1,3-dioxolan-2-yl | viscous oil |

-continued $$\begin{array}{c} \text{OH} \\ | \\ \text{R}-\text{C}-\left(\begin{array}{c}\text{CH}_3\\|\\\text{C}\\|\\\text{CH}_3\end{array}\right)_n-\text{Het} \\ | \\ \text{CH}_2 \\ | \\ \text{Az} \end{array}$$ (Ia)

| Example No. | R | Az | n | Het | Melting point (°C.) or $n_D^{20}$ |
|---|---|---|---|---|---|
| 66 | naphthyl-O-CH₂- | -N(pyrazole)- | 1 | 1,3-dioxolane | 126 |
| 67 | 4-Cl-3-CH₃-C₆H₃-O-CH₂- | -N(pyrazole)- | 1 | 1,3-dioxolane-C₃H₇ | viscous oil |
| 68 | 4-Cl-C₆H₄- | -N(1,2,4-triazole)- | 1 | 1,3-dioxolane-C₂H₅ | viscous oil |
| 69 | 4-Cl-3-CH₃-C₆H₃-O-CH₂- | -N(1,2,4-triazole)- | 1 | 1,3-dioxolane-C₃H₇ | viscous oil |
| 70 | 4-Cl-2-CH₃-C₆H₃-O-CH₂- | -N(1,2,4-triazole)- | 1 | 1,3-dioxolane-C₃H₇ | viscous oil |
| 71 | 4-Cl-2-CH₃-C₆H₃-O-CH₂- | -N(pyrazole)- | 1 | 1,3-dioxolane-C₃H₇ | viscous oil |
| 72 | naphthyl-O-CH₂- | -N(1,2,4-triazole)- | 1 | 1,3-dioxolane | viscous oil |
| 73 | naphthyl-O-CH₂- | -N(1,2,4-triazole)- | 0 | CH₃-1,3-dioxane | 96-98 |

-continued (Ia)

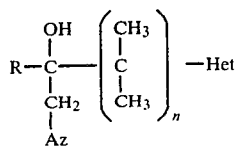

| Example No. | R | Az | n | Het | Melting point (°C.) or $n_D^{20}$ |
|---|---|---|---|---|---|
| 74 | naphthyl-O-CH₂- | -N(CH=N)imidazole | 0 | CH₃-C(CH₂O)₂ (dioxane, methyl) | 148-51 |
| 75 | biphenyl-O-CH₂- | -N(N=CH-N=CH) triazole | 0 | CH₃-C(CH₂O)₂ | 113-15 |
| 76 | biphenyl-O-CH₂- | -N(CH=CH-N=CH) imidazole | 0 | CH₃-C(CH₂O)₂ | 167-71 |
| 77 | biphenyl-CH=CH- | -N(N=CH-N=CH) triazole | 1 | dioxolane-CH₂-C₂H₅ | viscous oil |
| 78 | biphenyl-CH=CH- | -N(CH=CH-N=CH) imidazole | 1 | dioxolane-CH₂-C₂H₅ | 132-35 |
| 79 | biphenyl-CH₂-CH₂- | -N(N=CH-N=CH) triazole | 1 | dioxolane-CH₂-C₂H₅ | viscous oil |
| 80 | biphenyl-CH₂-CH₂- | -N(CH=CH-N=CH) imidazole | 1 | dioxolane-CH₂-C₂H₅ | viscous oil |
| 81 | 4-Cl-C₆H₄- | -N(CH=CH-N=CH) imidazole | 1 | dioxolane-CH₂-C₂H₅ | viscous oil |
| 82 | biphenyl- | -N(N=CH-N=CH) triazole | 1 | dioxolane-CH₂-C₂H₅ | viscous oil |

-continued

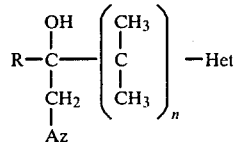 (Ia)

| Example No. | R | Az | n | Het | Melting point (°C.) or $n_D^{20}$ |
|---|---|---|---|---|---|
| 83 | 4-Cl, 2-CH₃ phenoxymethyl (H₃C top, Cl left) | 1,2,4-triazol-1-yl | 1 | 4-methyl-1,3-dioxolan-2-yl | viscous oil |
| 84 | 4-Cl, 2-CH₃ phenoxymethyl | imidazol-1-yl | 1 | 4-ethyl-1,3-dioxolan-2-yl | viscous oil |
| 85 | 4-Cl, 2-CH₃ phenoxymethyl | 1,2,4-triazol-1-yl | 1 | 4-methyl-1,3-dioxolan-2-yl | viscous oil |
| 86 | 4-Cl, 2-CH₃ phenoxymethyl | imidazol-1-yl | 1 | 4-methyl-1,3-dioxolan-2-yl | viscous oil |
| 87 | 2,4-dichlorophenyl | 1,2,4-triazol-1-yl | 1 | 1,3-dioxolan-2-yl | viscous oil |
| 88 | 2,4-dichlorophenyl | imidazol-1-yl | 1 | 1,3-dioxolan-2-yl | 138 |
| 89 | 4-tert-butylphenyl | 1,2,4-triazol-1-yl | 1 | 1,3-dioxolan-2-yl | viscous oil |
| 90 | 4-tert-butylphenyl | imidazol-1-yl | 1 | 1,3-dioxolan-2-yl | 164–66 |

NDS = 1,5-napthalenedisulphonic acid

USE EXAMPLES

The substances shown below are employed as comparison compounds in the use examples which follow:

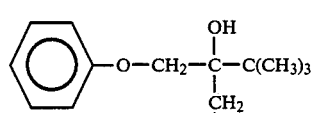 (A)

-continued

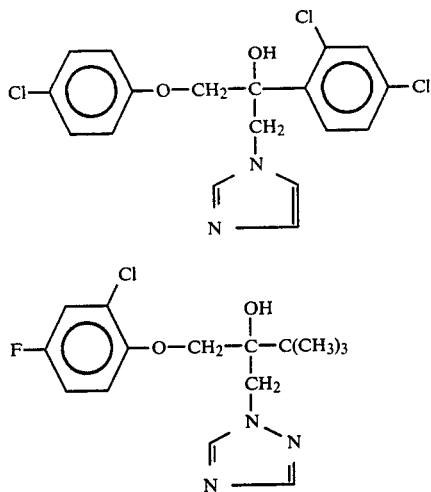

EXAMPLE A

Puccinia test (wheat) / protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are inoculated with a spore suspension of Puccinia recondita in a 0.1% strength aqueous agar solution. After the spore suspension has dried on, the plants are sprayed with the preparation of active compound until dew-moist. The plants remain in an incubation cabinet at 20° C. and 100% relative atmospheric humidity for 24 hours.

The plants are placed in a greenhouse at a temperature of about 20° C. and a relative atmospheric humidity of about 80% in order to promote the development of rust pustules.

Evaluation is carried out 10 days after the inoculation.

In this test, a clearly superior activity compared with the prior art is shown, for example, by the compounds according to the following preparation examples: 12, 13, 25, 10, 23, 8, 11, 21, 24, 7, 19, 9, 22, 5, 20 and 14.

EXAMPLE B

Botrytis test (beans)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar covered with Botrytis cinerea are placed on each leaf. The inoculated plants are placed in a darkened humidity chamber at 20° C. 3 days after the inoculation, the size of the infected spots on the leaves is evaluated.

In this test, a clearly superior activity compared with the prior art is shown, for example, by the compounds according to the following preparation examples: 11, 21, 24, 7, 19 and 5.

It will be understood that the specification and examples are illustrative but not limitative of the present invention and that other embodiments within the spirit and scope of the invention will suggest themselves to those skilled in the art.

What is claimed is:

1. A heterocyclyl-hydroxyalkyl-azolyl derivative of the formula

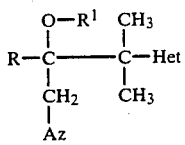

in which
Az represents 1,2,4-triazol-1-yl, 1,2,4-triazol-4-yl or imidazol-1-yl,
Het represents dioxolan-2-yl or 1,3-dioxanyl, each of which is optionally substituted by identical or different substituents selected from the group consisting of alkyl with 1 to 4 carbon atoms, and phenyl and phenoxyalkyl with 1 to 4 carbon atoms in the alkyl part, each of which is optionally substituted on the phenyl by identical or different substituents selected from the group consisting of halogen, alkyl with 1 to 4 carbon atoms, alkoxy and alkylthio with in each case 1 or 2 carbon atoms and halogenoalkyl, halogenoalkoxy and halogenoalkylthio with in each case 1 or 2 carbon atoms and 1 to 5 identical or different halogen atoms;
R represents straight-chain or branched alkyl with 1 to 7 carbon atoms, or phenyl, phenylalkyl with 1 to 4 carbon atoms in the alkyl part, phenoxy- or phenylthio-alkyl with in each case 1 to 4 carbon atoms in the alkyl part or phenylethenyl, each of which is optionally substituted on the phenyl by identical or different substituents selected from the group consisting of halogen, alkyl with 1 to 4 carbon atoms, alkoxy and alkylthio with in each case 1 or 2 carbon atoms, nitro, halogenoalkyl, halogenoalkoxy and halogenoalkylthio with in each case 1 or 2 carbon atoms and 1 to 5 identical or different halogen atoms, hydroximinoalkyl with 1 to 4 carbon atoms, alkoximinoalkyl with 1 to 4 carbon atoms in each alkyl part, and phenyl, phenoxy, benzyl and benzyloxy, each of which is optionally substituted by halogen or alkyl with 1 or 2 carbon atoms; or R represents cycloalkyl with 5 to 7 carbon atoms, which is in each case optionally monosubstituted or polysubstituted by identical or different alkyl radicals with 1 to 4 carbon atoms, or cycloalkyl-methyl or -ethyl with 5 to 7 carbon atoms in the cycloalkyl part, or cyclohexylethenyl, or, alkenyl with 2 to 6 carbon atoms, 2-furyl, naphthyloxymethyl, 1,2,4-triazol-1-yl-methyl, 1,2,4-triazol-4-yl-methyl, imidazol-1-yl-methyl or pyrazol-1-yl-methyl,
R' represents hydrogen, alkyl which has 1 to 4 carbon atoms and is optionally substituted by phenyl, it being possible for the phenyl radical to be substituted by the substituents on phenyl mentioned under R, or alkenyl with 2 to 4 carbon atoms,
or an addition product thereof with an acid or metal salt.

2. A heterocyclyl-hydroxyalkyl-azolyl derivative of the formula

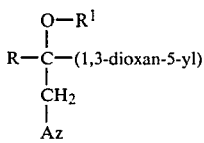

in which
Az represents 1,2,4-triazol-1-yl, 1,2,4-triazol-4-yl or imidazol-1-yl; the 1, 3- dioxan-5-yl is optionally substituted by identical or different substituent selected from the group consisting of alkyl with 1 to 4 carbon atoms, and phenyl and phenoxyalkyl with 1 to 4 carbon atoms, and phenyl and phenoxyalkyl with 1 to 4 carbon atoms in the alkyl part, each of which is optionally substituted on the phenyl by identical or different substituents selected from the group consisting of halogen, alkyl with 1 to 4 carbon atoms, alkoxy and alkylthio with in each case 1 or 2 carbon atoms and halogenoalkyl, halogenoalkoxy and halogenoalkythio with in each case 1 or 2 carbon atoms and 1 to 5 identical or different halogen atoms;
R represents straight-chain or branched alkyl with 1 to 7 carbon atoms, or phenyl, phenylalkyl with 1 to 4 carbon atoms in the alkyl part, phenoxy- or phenylthio-alkyl with in each case 1 to 4 carbon atoms in the alkyl part or phenylethenyl each of which is optionally substituted on the phenyl by identical or different substituents selected from the group consisting of halogen, alkyl with 1 to 4 carbon atoms, alkoxy and alkylthio with in each case 1 or 2 carbon atoms, nitro, halogen alkyl, halogenoalkoxy and halogenoalkylthio with in each case 1 or 2 carbon atoms and 1 to 5 identical or different halogen atoms, hydroximinoalkyl with 1 to 4 carbon atoms, alkoximinoalkyl with 1 to 4 carbon atoms in each alkyl part, and phenyl, phenoxy, benzyl and benzyloxy, each of which is optionally substituted by halogen or alkyl with 1 or 2 carbon atoms; or R represents cycloalkyl with 5 to 7 carbon atoms, which is in each case optionally monosubstituted or polysubstituted by identical or different alkyl radicals with 1 to 4 carbon atoms, or cycloalkyl-methy or -ethyl with 5 or 7 carbon atoms in the cycloalkyl part, or cyclothexylethenyl, or, alkenyl with 2 to 6 carbon atoms, 2-furyl, naphthyloxymethyl, 1,2,4-triazol-1-yl-methyl, 1,2,4-triazol-4-yl-methyl, imidazol-1-yl-methyl or pyrazol-1-yl-methyl,
R' represents hydrogen, alkyl which has 1 to 4 carbon atoms and is optionally substituted by phenyl, it being possible for the phenyl radical to be substituted by the substituents on phenyl mentioned under R, or alkenyl with 2 to 4 carbon atoms.
or an addition product thereof with an acid or metal salt.

3. A compound or addition product according to claim 1, wherein
Het represents dioxolan-2-yl, 1,3-dioxan-5-yl or 1,3-dioxan-2-yl, each of which is optionally mono-, di- or tri-substituted by identical or different substituents selected from the group consisting of methyl, ethyl, n-propyl, isopropyl propyl and phenyl and phenoxymethyl, each of which is optionally mono-, di- or tri-substituted by identical or different substituents from the group consisting of fluorine, chlorine, methyl, trifluoromethyl and trifluoromethoxy;
R represents tert.-butyl, trimethyl-propyl or tetramethyl-propyl, or phenyl, benzyl, phenethyl, phenoxymethyl, phenylthiomethyl or phenethenyl each of which is optionally mono-, di- or tri-substituted by identical or different substituents selected from the group consisting of fluorine, chlorine, methyl, trifluoromethyl, trifluoromethoxy, trifluoromethylthio, hydroximinomethyl, 1-hydroximinoethyl, methoximinomethyl, 1-methoximinoethyl, and phenyl, phenoxy, benzyl and benzyloxy, each of which is optionally substituted by chlorine and/or methyl; or R represents cyclohexyl, cyclohexylmethyl, cyclohexylethyl or cyclohexylethenyl each of which is optionally mono- or di-substituted by identical or different substituents from the group consisting of methyl, ethyl and isopropyl; or R represents allyl, dimethylpropentl, 2-furyl, napthyloxymethyl, 1,2,4-triazol-yl-methyl, 1,2,4-triazol-4-yl-methyl, imidazol-1-yl-methyl or pyrazol-1-yl-methyl; and R' represents hydrogen, methyl, 4 chlorobenzyl or allyl.

4. A compound according to claim 1, wherein such compound is 1-(4-chlorophenyl)-4-(1,3-dioxolan-2-yl)-4-methyl-3-(1,2,4-triazol-1-yl-methyl)-3-pentanol of the formula

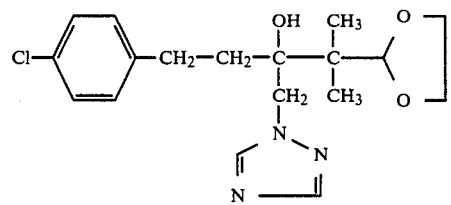

or an addition product thereof with an acid or metal salt.

5. A compound according to claim 2, wherein such compound is 1-(4-chlorophenyl)-4-(1,2,4-triazol-1-yl)-3-(5-methyl-1,3- dioxan-5-yl)-3-butanol of the formula

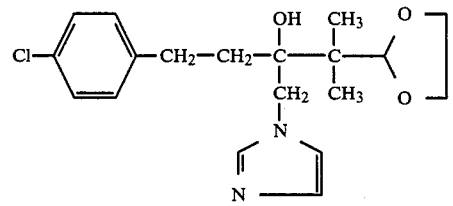

or an addition product thereof with an acid or metal salt.

6. A compound according to claim 1, wherein such compound is 1-(4-chlorophenyl)-4-(1,3-dioxolan-2-yl)-3-(imidazol-1-yl-methyl)-4-methyl-3-pentanol of the formula

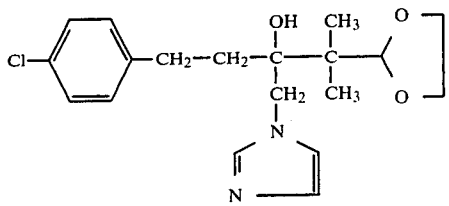

or an addition product thereof with an acid or metal salt.

7. A fungicidal composition comprising a fungicidally effective amount of a compound or addition product according to claim 1 in admixture with a diluent.

8. A fungicidal composition comprising a fungicidally effective amount of a compound or addition product according to claim 2 in admixture with a diluent.

9. A method of combating fungi which comprises administering to such fungi or to a habitat thereof a fungicidally effective amount of a compound or addition product according to claim 1.

10. A method of combating fungi which comprises administering to such fungi or to a habitat thereof a fungicidally effective amount of a compound or addition product according to claim 2.

11. The method according to claim 9, wherein such compound is
1-(4-chlorophenyl)-4-(1,3-dioxolan-2-yl)-4-methyl 3-(1,2,4-triazol-1-yl-methyl)-3-pentanol or
1-(4-chlorophenyl)-4-(1,2,4-triazol-1-yl)-3-(5-methyl-1,3-dioxan-5-yl)-3-butanol,
or an addition product thereof with an acid or metal salt.

12. A method according to claim 9, wherein such compound is
1-(4-chlorophenyl)-4-(1,2,4-triazol-1-yl)-3-(5-methyl-1,3-dioxan-5-yl)-3-butanol,
or an addition product thereof with an acid or metal salt.

* * * * *

UNITED STATES PATENT AND TRADEMARK OFFICE
CERTIFICATE OF CORRECTION

PATENT NO. : 4,639,462
DATED : January 27, 1987
INVENTOR(S) : Wolfgang Krämer, et al.

Page 1 of 3

It is certified that error appears in the above-identified patent and that said Letters Patent is hereby corrected as shown below:

| | |
|---|---|
| Title Page,"Abstract", line 11 | After "substituted" delete "phenoxyalky" and substitute --phenoxyalkyl-- |
| Col. 1, lines 5 and 6 | Delete "hydroxyalk-ylazdylyl" and substitute --hydroxyalkyl-azolyl-- |
| Col. 1, line 7 | Before "processes," delete "sveral" and substitute --several-- |
| Col. 1, line 11 | Delete "2butanol" and substitute --2-butanol-- |
| Col. 1, line 12 | Before "(1,2,4-" insert -- - -- |
| Col. 2, line 59 and Col. 2, line 61 | Before "-methyl" delete "ly" and substitute --yl-- |
| Col. 2, line 62 | After "imidazol-1-" delete "ly" and substitute --yl-- |
| Col. 3, line 3 | After "triazol-1-" delete "ly" and substitute --yl-- |
| Col. 3, line 3 | After "triazol-4-" delete "ly" and substitute --yl-- |
| Col. 3, line 4 | After "imidazol-1-" delete "ly" and substitute --yl-- |
| Col. 3, line 20 | After "as" insert --,-- |
| Col. 3, line 27 | After "optionally" delete "mono-sustituted" and substitute --monosubstituted-- |
| Col. 3, line 40 | Delete "ach" and substitute --each-- |
| Col. 3, line 43 | Delete "opticnally" and substitute --optionally-- |
| Col. 3, line 47 | After first "or" correct spelling of --cyclohexylethenyl-- |

UNITED STATES PATENT AND TRADEMARK OFFICE
CERTIFICATE OF CORRECTION

PATENT NO. : 4,639,462
DATED : January 27, 1987
INVENTOR(S) : Wolfgang Krämer, et al.

Page 2 of 3

It is certified that error appears in the above-identified patent and that said Letters Patent is hereby corrected as shown below:

| | |
|---|---|
| Col. 3, line 49 | After "2-furyl" delete "napthylozymethyl" and substitute --napthyloxymethyl-- |
| Col. 3, line 50 | After "triazol-1" delete "1y" and substitute --yl-- |
| Col. 3, line 50 | After "triazol-4" delete "1y" and substitute --yl-- |
| Col. 3, line 51 | After "imidazol-1-" delete "1y" and substitute --yl-- |
| Col. 13, line 24 | Before "first "of" delete "prepaation" and substitute --preparation-- |
| Col. 14, line 25 | Before "as" delete "equired" and substitute --required-- |
| Col. 14, lin 25 | Delete "stating" and substitute --starting-- |
| Col. 14, line 27 | Before "European" delete "]" and substitute --[-- |
| Col. 14, line 56 | Delete "(60)" and substitute --($\alpha$)-- |
| Col. 15, line 4 | Delete "knowp" and substitute --known-- |
| Col. 16, line 3 | After "between" delete "60°OC." and substitute --60°C.-- |
| Col. 22, line 43 | After "and" delete "0" and insert --50-- |
| Col. 23, line 30 | Before "-dioxolan" delete "13" and substitute --1,3-- |
| Col. 23, line 56 | After "oil," insert --which-- |

UNITED STATES PATENT AND TRADEMARK OFFICE
CERTIFICATE OF CORRECTION

PATENT NO. : 4,639,462

DATED : January 27, 1987

INVENTOR(S) : Wolfgang Krämer, et al.

It is certified that error appears in the above-identified patent and that said Letters Patent is hereby corrected as shown below:

Col. 31-32, Example No. 41 and Col. 33-34, Example No. 50     Delete formula under "Az" and substitute 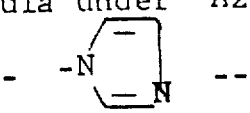

Col. 40, Example No. 76     Under "Melting point" column, delete "167-71" and substitute $_1$ --169-71--

Col. 44, lines 15-20 and Col. 45, lines 6 to 13     In the formula delete "$R^1$" and substitute --R'--

Col. 45, line 50     Delete "methy" and substitute --methyl--

Signed and Sealed this

Seventh Day of June, 1988

Attest:

DONALD J. QUIGG

Attesting Officer     Commissioner of Patents and Trademarks